United States Patent [19]

Blass

[11] Patent Number: 5,053,396
[45] Date of Patent: Oct. 1, 1991

[54] THERAPEUTIC COMPOSITION

[76] Inventor: David H. Blass, 7 Hereford Mansions, Hereford Street, London W2 5BA, Great Britain

[21] Appl. No.: 562,425

[22] Filed: Aug. 1, 1990

Related U.S. Application Data

[63] Continuation of Ser. No. 44,402, filed as PCT EP86/00492 on Aug. 21, 1985, published as WO87/01285 on Mar. 12, 1987, abandoned.

[51] Int. Cl.$^5$ .............................................. A61K 31/00
[52] U.S. Cl. ...................................... 514/45; 514/46
[58] Field of Search ...................... 536/23, 26; 514/45, 514/50, 51, 52

[56] References Cited

U.S. PATENT DOCUMENTS

| 3,829,569 | 8/1971 | Rice | 514/165 |
| 4,182,770 | 1/1980 | Behpour et al. | 514/398 |

FOREIGN PATENT DOCUMENTS

23812 10/1966 France.

OTHER PUBLICATIONS

Heikmian et al., Journal on Studies of Alcoholism, 06/1966, 27(2), pp. 214–220.
Vidal, Dictionnaire Vidal, p. 2263 'Vitaspran'; p. 1369 'Nicobion Aspirine'(1964), English Translation of AR 1.
English Translation of AL, International Search Report—International Application No. PCT/EP86/00492.

*Primary Examiner*—Johnnie R. Brown
*Assistant Examiner*—James O. Wilson
*Attorney, Agent, or Firm*—Sterne, Kessler, Goldstein & Fox

[57] ABSTRACT

A therapeutic composition and a method for the treatment of the acute and/or chronic symptoms associated with the excessive ingestion or inhalation of alcohols, most particularly ethanol in the form of alcoholic beverages. The therapeutic composition comprises an analgesic, nicotinamide and/or NAD, the nicotinamide and/or NAD being present in an amount of at least 7% by weight of the analgesic. The composition can further comprise additional water-soluble vitamins, and antacid component, an electrolyte salt replacement component, trace metal ions, and antihistaminic component, fructose, an alkaloid component and usual additives like sweetening agents, effervescent components, carriers, fillers, coloring agents, a.s.o. The composition is administered in a single dose either before going to sleep or the morning after.

28 Claims, No Drawings

THERAPEUTIC COMPOSITION

This application is a continuation of application Ser. No. 07/044,402, filed as PCT EP86/00492 on Aug. 21, 1985, published as WO87/01285 on Mar. 12, 1987, now abandoned.

The present invention relates to a therapeutic composition for the treatment of the acute and/or chronic symptoms associated with the excessive ingestion or inhalation of alcohols, most particularly ethanol in the form of alcoholic beverages and to a method for treating such symptoms.

It is well known that the symptoms produced by the excessive, i.e. intoxicating, intake of ethanol are unpleasant, particularly in the post-exhilaration or "hangover" stage. Such symptoms include overwheming physical and mental fatigue, vomiting, nausea, loss of appetite, tremors of the head and limbs (the "shakes"), abdominal palpitations, weakness in the joints, a general confusion and lack of co-ordination, respiratory difficulties, sleeplessness and headache. In more extreme cases, the toxic effects of alcohol can lead to coma, circulatory collapse, convulsions and death.

It is believed that between 11 and 40 million instances of the above symptoms occur in the United Kingdom each year, and although the majority of sufferers experience relatively mild symptoms, mortality as a direct or indirect result is not unknown.

Although the majority of cases of alcoholic intoxication occur as a direct result of the use of alcohol in a liquid form as a recreational or escapist drug, there is occasional accidental exposure to alcohol vapour.

Chronic exposure to alcohol causes more marked symptoms. It is believed that the chronic symptoms of alcoholism can begin to appear at consumption levels which are considered acceptable in certain parts of society, such as an average consumption of about 10 liters of beer per week.

Following chronic exposure to alcohol the following symptoms may occur: alcoholic polyneuritis, tremor, muscle weakness and incoordination severe enough to prevent use of the extremities. The above neuromuscular symptoms are often accompanied by personality disorders, ranging from mild effects such as loss of emotional control leading to mania or depression to severe effects such as dementia, alcoholic psychosis, hallucinations and delerium tremens ("DT").

The above effects are thought to detract from the use of ethanol as a socially acceptable drug, place a severe burden on health and social services, reduce work efficiency and increase absenteeism.

It is believed that the toxic effects of alcohols, especially ethanol are caused by one or more of the following:

(a) Accumulation of acetaldehyde, a product of the oxidation of ethanol which although broken down at a rate greater than that of the oxidation of ethanol, is more toxic. Ethanol is converted into acetaldehyde under the action of the enzyme alcohol dehydrogenase, and acetaldehyde is further oxidised into acetic acid by the same enzyme, and by aldehyde dehydrogenase.

(b) Pertubation of blood-sugar levels, by promotion of glycogenolysis (breakdown of glycogen and release of glucose). This elevated blood-sugar levels and eventually depletes liver glycogen. Chronic exposure to ethanol can result in acute hypoglycemia, especially if the patient is in a poor nutritional state, unless this liver glycogen can be replaced.

(c) Fatigue from exertion, often to the point of neuromuscular exhaustion, results when the judgement is impaired and physical activity continues beyond the point at which a reasonable man would stop. One effect of this intense activity is that anaerobic metabolism may occur and it is believed that, in consequence, significant levels of lactic acid may accumulate.

(d) Significant dehydration, as a result of the suppressive effect of ethanol on the anti-diuretic hormone, vasopressin, to elevate urine production.

(e) Nausea, due to disturbance of intestinal tract and the bacterial life-forms occupying portions of the tract.

A wide variety of treatments have been proposed for both the acute and chronic symptoms of alcohol intoxication. The following are some of the remedies suggested in the prior art:

Administration of analgesics such as acetylsalicylic acid, sedatives such as paraldehyde or tranquilizers such as chlorpromazine. Nicotinamide administered intravenously in a dosage of more than 100 mg to control spastic muscular reactions. Insulin shock treatment. Vitamin B complex administered to counter the effects of poor nutrition, and the intramuscular or sublingual administration of nicotinamide adenylate or nicotinamide ascorboadenylate to dispose of tremors.

The solutions of the prior art have been found to be rather ineffective in treating hangovers. Many of the compounds either must be administered under skilled medical supervision or have unpleasant side effects. Consequently, the use of such compounds would place an unacceptable burden on health services. Furthermore, many of the substances proposed for use in the treatment of alcohol intoxication are controlled substances which are or can be addictive to the user.

It is an object of the present invention to provide a therapeutic composition and a method for the treatment of the acute and/or chronic symptoms associated with the excessive ingestion or inhalation of alcohols without the problems of the prior art.

According to one aspect of the present invention there is provided a therapeutic composition for the treatment of the symptoms associated with the excessive intake of alcohol, comprising (a) at least one analgesic;
(b) nicotinamide and/or nicotinamide adenine dinucleotide (NAD);

the amount of component (b) being at least 7% preferably at least 10% and preferably considerably over 10% by weight of component (a) and further optionally comprising one or more of the following components:

(c) at least one additional water-soluble vitamin;
(d) an antacid component;
(e) an electrolyte salt replacement component;
(f) trace metal ions;
(g) at least one antihistamine;
(h) fructose;
(i) at least one alkaloid having a stimulating effect;
(j) usual additives according to the form of administration, like sweetening agents, flavoring agents, coloring agents, effervescent components, carriers, fillers, a.s.o.

It is believed that intake of nicotinamide and/or NAD aids in the breakdown of alcohol and its breakdown intermediates. Moreover, it is known that coenzymes are generally involved in oxidative metabolism and it is thought that the administration of the coenzyme NAD or of nicotinamide as precursor of NAD has a generally restorative and invigorating effect upon the body which not only accelerates the process of alcohol breakdown but protects tissues against the toxic effects both of alcohol and its breakdown products. In addition to the effects of the co-enzyme per se, there is a therapeutic synergistic action between the compulsory components of the composition which action is increased by the addition of one or more optional components, especially of water-soluble vitamins. Typically, water-soluble vitamins which are advantageous in the composition are selected from the group comprising pantothenic acid, riboflavin, pyridoxine hydrochloride, thiamine hydrochloride, and ascorbic acid.

Nicotinamide is a precursor of nicotinamideadenine dinucleotide (NAD, also known as diphosphopyridine nucleotide (DNP) and co-enzyme I) which is an essential co-factor for the oxidation of ethanol to acetaldehyde and then to acetic acid by the enzymes alcohol dehydrogenase and aldehyde dehydrogenase. NAD is reduced during this oxidation to yield NADH. The activity of this enzyme is probably rate limiting for alcohol breakdown. It is suggested that an increase in the size of the NAD pool accelerates this breakdown. It is further suggested that an enlarged NAD pool assists in the rapid breakdown of latic acid, by the enzyme lactate dehydrogenase, which also depends on NAD for its function. For quick action as desired in certain cases and especially for so-called "morning-after" compositions, the composition can comprise NAD per se, alone or in admixture with nicotinamide. This latter compound on the other hand has the advantage of being less sensitive to gastric fluids and of forming NAD in a continuous protracted manner so that the NAD pool is continuously replenished.

Riboflavin is a precursor of flavin mononucleotide (FMN) and flavin adenine dinucleotide which are involved in the reoxidation of NADH. It is suggested that increased levels of riboflavin will result in a higher turnover of NADH and that this will have an effect upon the rate of reactions in which NAD is consumed.

Pantothenic acid is a precursor of co-enzyme A, which is the most prominent acyl group transfer co-enzyme in living systems and has one particular activity of combining with acetate to form acetyl-CoA, an important metabolic intermediate. It is suggested that elevated levels of pantothenic acid may enhance the restoration of normal acetate levels, and assist in the elimination or decomposition of alcohol.

Pyridoxine hydrochloride is the precursor of pyridoxal phosphate which is in turn the most striking co-enzyme in terms of the multiplicity of reactions in which it is involved. One important function of this co-enzyme is in the maintenance of serotonin levels in the brain. It is known that variations in serotonin levels can cause changes of mood and perception. It is known that pyridoxine hydrochloride is useful in the treatment of oestrogen induced depression, and it is suggested that this vitamin may help in the treatment of alcohol induced depression. Pyridoxine is also known to be required in the synthesis of NAD but it is not thought that this is of major importance in the present context.

Thiamine hydrochloride is a precursor of thiamine pyrophosphate, which is known to prevent polyneutritis and beriberi. It is here present as a restorative for the central nervous system. The possibility of the use of a lipid-soluble thiamine derivate with an enhanced ability to cross the blood-brain barrier is not hereby excluded.

Ascorbic acid (vitamin C) is believed to protect against the toxic effects of high levels of acetaldehyde.

The analgesic can be chosen from a wide range of compounds known in the art, especially non-opiate analgesics, non-steroidal anti-inflammatory agents, opioid analgesics such as morphine and derivatives thereof or compounds acting on opiate receptors or mixtures thereof. Acetylsalicylic acid, ibuprofen, [α-methyl-4-(2-methylpropyl)-benzine acetic acid] and fenoprofen are especially recommended. Some useful analgesis are e.g.:

Diflunisal
Sulindac
Fenoprofen calcium
Acetaminophen
Mefanamic acid
Naproxen
Codein
Dextropropoxyphene.HCl
Meperidine In addition to the above compounds, it is proposed to include fructose in the composition. It is known that fructose is particularly useful in the elimination of alcohol. The mechanism for this is not fully understood, however, it is believed that there is an acceleration of glycolysis in the presence of fructose which may be the relevant factor. Moreover, it is thought that products of the metabolism of fructose may influence that rate of reoxidation of NADH in situ on the ADH enzyme or elsewhere, and therefore increase both the turnover rate of this enzyme and the turnover rate of NAD dependent pathways. Moreover fructose has a strong sweetening capacity and it is able to mask certain undesired tastes of other components.

In addition to the above compounds, it has proven to be advantageous to include an antihistamine in the medicament. It is believed that an allergenic reaction to some constituents of alcoholic drinks makes hangovers worse for some people, and therefore it is proposed to add an antihistamine to the medicament. Most antihistamines in addition have more or less soporific effect and some in addition have a useful antinausea effect which further contributes to the usefullness of the present invention. Suitable antihistamines are e.g. promethazine-hydrochloride, chlorpheniramine maleate, Diphenhydramine hydrochloride
Dimenhydrinate
Carboxamine maleate
Pyrilamine maleate
Tripelennamine hydrochloride (or citrate)
Brompheniramine maleate
Hydroxizine hydrochloride (or pamoate)
Cyclizine hydrochloride (or lactate)
Meclizine hydrochloride
Buclizine hydrochloride Additionally it is believed that a specific antinausea agent could be added to the composition, e.g.

Prochlorperazine
Metoclopramide HCl.

A further additional component of the composition can be an antacid component, like Magnesium oxide
Sodium bicarbonate
Potassium bicarbonate
Magnesium hydroxide
Calcium carbonate
Sodium citrate In addition to the above compounds, it is proposed to include an electrolyte replacement component comprising at least one of the cations potassium, sodium, magnesium or calcium. Or the anions bicarbonate and carbonate or phosphate. These metals can also be present as salts of organic acids, e.g. glucuronic acid, levulinic acid or ascorbic acid, or as aminoacid chelates.

Trace metals like manganese, iron, chromium and copper, preferably also in the form of salts of organic acids or as amino-acid chelates, can be present in small quantities as metabolic adjuncts. The presence of Zn++ ions can further be very valuable. These help for the function of NAD as oxidant of alcohol. Zinc ions can be added to the composition in the form of salts or of amino acid chelates.

In addition to the above compounds, it is proposed to include an alkaloid having stimulating effects comprising at least one of caffein, theobromine or theophylline in the composition, especially if it is administered as a "morning after" medicament. If the composition is administered before going to sleep the addition of caffein or a like alkaloid may cause minor problems by keeping the patient awake if the medicament is adminsitered before sleep. It is proposed that the caffein or like alkaloid might be included in a separate pill or powder in a common packaging, or that two types of clearly identifiable medicament might be prepared, one with the alkaloid but without soporific antihistamine as "morning-after" composition and one without alkaloid but containing such an antihistamine for administering before going to sleep.

In order that the invention may be further understood and without limitation, the following examples of the composition according to the present invention is given. The components as indicated are mixed together and formulated to the desired therapeutic compositions in a manner well known in the art.

Preferred and minimum dosages for the components to be included within the composition (per dose) are indicated below without limiting the invention.

| Component | Preferred dosage | Range |
|---|---|---|
| Acetylsalicylic acid | 600-900 mg | 300-1000 mg |
| or Ibuprofen | 150-200 mg | 100-300 mg |
| or Fenoprofen calcium | 300-600 mg | 200-800 mg |
| Nicotinamide | 300-500 mg | 70-1500 mg |
| NAD | 100-200 mg | 70-300 mg |
| Pantothenic acid | 100-400 mg | 50-500 mg |
| Riboflavin | 30-60 mg | 5-100 mg |
| Pyridoxine HCl | 30-60 mg | 5-100 mg |
| Thiamine HCl | 70-150 mg | 50-600 mg |
| Ascorbic acid | 250-500 mg | 100-800 mg |
| Fructose | 5000 mg | 2000-15000 mg |
| Promethazine HCl | 25 mg | 10-50 mg |
| or Chlorpheniramine maleate | 4 mg | 2-6 mg |
| Sodium bicarbonate | — | 0-4000 mg |
| Potassium bicarbonate | — | 0-4000 mg |
| Magnesium carbonate | — | 0-4000 mg |
| or Magnesium oxide or hydroxyde | — | 0-4000 mg |
| Calcium carbonate | — | 0-4000 mg |
| Citric acid | 1200-1800 mg | 0-4000 mg |
| Zinc ions | 1,5 mg | 0,5-20 mg |
| Iron ions | 10 mg | 5-30 mg |
| Mangenese ions | 0,6 mg | 0,3-1,0 mg |
| Chromium ions | 1 mcg | 1 mcg |
| Sweetening or flavouring agents and other additives | as required | |

Any of the metals mentioned in this specification could be present wholly or partly as the salts of gluconic, levulinic, ascorbic, citric or phosphoric acids, or any other suitable acids, where this would be advantageous. They could also be present wholly or partly as amino acid chelates.

Thamine could be present as a lipid soluble derivative or derivatives. This might also be suitable form of some of the other components.

If NAD is used, it is advisable to put it in a form suitable for sublingual absorption, or as enteric coated granules, or in some other form which will ensure that it is effectively absorbed.

NAD could also be included in the remedy in the form of an ascorbic acid derivative. The above strictures on presentation would still apply.

Although minimum dosages are given for the preferred compounds, it is not considered necessary that the composition should comprise all of these compounds.

In the following examples the indicated composition is intended for 1000 doses. Compositions to be taken before going to sleep are administered only once in one single dose. The "morning after" -compositions are also to be taken only as one dose directly after waking up or together with a light breakfast.

EXAMPLE 1

| | |
|---|---|
| Acetylsalicylic acid | 900 g |
| Nicotinamide | 500 g |
| Sodium bicarbonate | 1176 g |
| Potassium bicarbonate | 1400 g |
| Citric acid | 2100 g |
| Fructose | 5000 g |
| Chlorpheniramine maleate | 4 g |

The composition is presented in the form of a soluble powder or tablets in a ready-to-consume dosage form to be administered with a big glass of water or orange juice.

EXAMPLE 2

| | |
|---|---|
| Acetylsalicylic acid | 900 g |
| Nicotinamide | 500 g |
| Sodium bicarbonate | 756 g |
| Potassium bicarbonate | 900 g |
| Citric acid | 1260 g |
| Fructose | 3000 g |
| Promethazine HCl | 25 g |

With this reduced amount of effervescent couple present, the acetylsalicylic acid may need to be pretreated in some way to achieve solubilisation within a reasonable time, e.g. according to the method disclosed in British Patent 1.287.475.

EXAMPLE 3

Example 2 is repeated, but with the proportions of sodium and potassium bicarbonate changed to

| | |
|---|---|
| Sodium bicarbonate | 1680 g |
| Potassium bicarbonate | 900 g |

EXAMPLE 4

| | |
|---|---|
| Fenoprofen calcium | 600 g |
| Nicotinamide | 500 g |
| Sodium bicarbonate | 1512 g |
| Magnesium levulinate | 400 g |
| Fructose | 3000 g |

| | |
|---|---|
| Promethazine HCl | 25 g |

The components are formulated in the form of a soluble powder or tablets.

EXAMPLE 5

| | |
|---|---|
| Acetylsalicylic acid | 900 g |
| Nicotinamide | 500 g |
| Sodium bicarbonate | 1680 g |
| Potassium bicarbonate | 900 g |
| Citric acid | 2160 m |
| Thiamine | 120 g |
| Chelated zinc | 3 g (of element) |
| Magnesium gluconate | 300 g |
| Calcium gluconate | 300 g |
| Fructose | 5000 g |
| Chlorpheniramine maleate | 4 g |
| Sweetening and flavouring agents | as required |

The composition is presented as a soluble powder or tablets.

EXAMPLE 6

| | |
|---|---|
| Fenoprofen calcium | 600 g |
| Nicotinamide | 600 g |
| Magnesium gluconate | 650 g |
| Fructose | 4000 g |

This simple composition is presented as a soluble powder or tablets.

EXAMPLE 7

This is formulation to be taken "the morning after".

| | |
|---|---|
| Part A | |
| Acetylsalicylic acid | 900 g |
| Sodium bicarbonate | 2000 g |
| Potassium bicarbonate | 900 g |
| Citric acid | 2100 g |
| Caffein | 80 g |
| Fructose | 6000 g |
| Part B | |
| Fructose | 350 g |
| NAD | 200 g |
| Flavouring | trace |

Part A is prepared as a powder for solution.
Part B is prepared in a suitable carrier for sublingual absorption.

EXAMPLE 8

Example 6 is repeated, but replacing 600 g of the potassium bicarbonate in part A with 300 g of magnesium gluconate together with 300 g of calcium carbonate.

EXAMPLE 9

This is a simpler "morning after" -formulation, occupying less volume and therefore suitable for presentation as a pill to be swallowed.

| | |
|---|---|
| Ibuprofen | 250 g |
| NAD | 250 g |
| Caffein | 80 g |

Each dose could comprese 2 or 3 pills, possibly enteric coated.

EXAMPLE 10

An alternative formulation to the above, wich would be suitable for use either at night, or the morning after.

| | |
|---|---|
| Ibuprofen | 250 g |
| NAD | 200 g |
| Nicotinamide | 700 g |

This could also be provided as enteric coated pills.

EXAMPLE 11

Another formulation for the morning after.

| | |
|---|---|
| Ibuprofen | 250 g |
| Nicotinamide | 700 g |
| Caffein | 80 g |

This formulation can be provided as sugar coated pills. The sugar coating is composed of a relatively thick layer of fructose with appropriate surface protection, for example zein, which has the further advantage that it makes the pills easier to swallow since it is slippery when wet.

EXAMPLE 12

Another pill, either for the morning after or night time use.

| | |
|---|---|
| Fenoprofen calcium | 600 g |
| Nicotinamide | 500 g |
| Magnesium levulinate | 500 g |

This pill could be sugar coated, perhaps with fructose as in example 10. With a suitable sweetening agent (for example aspartame) it could alternatively be made up as a powder or tablets for solution.

EXAMPLE 13

The remedy in the form of a dragee or lozenge, to be sucked. For morning use.

| | |
|---|---|
| Fenoprofen calcium | 600 g |
| NAD | 200 g |
| Fructose | 2500 g |
| Flavouring | as required |

A suitable binding agent is employed to slow down the rate of solution in the mouth. It is considered that this may assist the absorption of the NAD. The addition of caffein 80 mg per dose is an option.

EXAMPLE 14

A dragee or lozenge, for administration before sleep.

| | |
|---|---|
| Fenoprofen calcium | 600 g |
| NAD | 200 g |

-continued

|   |   |
|---|---|
| Nicotinamide | 450 g |
| Magnesium gluconate | 200 g |
| Fructose | 2500 g |

The addition of suitable sweetening or flavouring agents may be desirable.

EXAMPLE 15

A syrup contains:

|   |   |
|---|---|
| Nicotinamide | 500 g |
| Fenoprofen calcium | 600 g |
| Magnesium gluconate | 300 g |
| Calcium gluconate | 100 g |
| Chlorpheniramine maleate | 4 g |
| Fructose | 12000 g |

The above mixture is made up in 15 liters of water. The fenoprofen could be replaced with paracetamol (1000 mg per dose). If this were done, then the amount of calcium gluconate could usefully be increased to 300 mg per dose.

The inclusion of a suitable preservative agent is advisable.

For one dose 15 ml are mixed with a large glass of water, or are swallowed undiluted.

All of these compositions gave excellent results in preventing or releaving the symptoms of hangover.

The test subjects were each provided with an amount of alcohol which they would normally expect would give them a hangover if they drank it. The alcohol was in the form of wine, beer or spirits with mixers. The subjects were allowed to choose which they preferred. They were requested to drink the supplied alcoholic beverages over a three hour period in the evening. In all cases the amounts of alcohol provided were enough to give an expected blood ethanol level of at least 90 mg/100 ml, and in many cases considerably higher than this. Subsequently the subjects were provided with one dose of one of the formulations mentioned above for night time use. The reports of the subjects concerning their wellbeing next morning showed that the remedy was effective in either preventing or reducing the hangover syndrome. The headache, tremor, vertigo and general malaise associated with hangover were either not present, or very much less severe than the subjects themselves would have anticipated. The sensations of weakness and fatigue associated with hangover were also either prevented or greatly reduced in severity. Corresponding results were obtained with those test subjects which took a "morning after"-formulation after waking up with severe problems next morning without having taken any of the formulations before going to sleep.

Although the invention may be preferably embodied as a single pill, other dosage forms, such as a soluble powder a dragee or lozenge, an effervescent composition, a syrup, a tincture, an elixir or suppositories are acceptable. It is envisaged that one or more of these or other forms of dosage in combination are acceptable, either to remove the problems of caffein dosage, or to increase the dosage of fructose.

For example, caffein could be presented in a separate pill which the user could discard if the medicament were being taken before sleep. Moreover, the content of acetylsalicylic acid could be present as a water-soluble powder for separate solution.

It is to be noted that the desired effect can only be achieved if the amount of component (b) is at least 7% by weight of component (a). Although considerably higher amounts of (b) have been used in the above examples and are believed to be more effective than lower amounts. However, valuable results can be obtained with any amounts over 7%, whereas amounts of less than 7% are considered as unsatisfactory in achieving the desired effect.

What is claimed is:

1. A therapeutic composition for the treatment of the symptoms associated with the excessive intake of alcohol, comprising:
   (a) an analgesic;
   (b) 70 to 1500 mg per unit dose of nicotinamide or 70 to 300 mg of nicotinamide adenine dinucleotide (NAD);
   wherein the amount of component (b) is 7% or greater by weight of component (a), further comprising one or more of the following components:
   (c) a water soluble vitamin selected from the group consisting of pantothenic acid, riboflavin, pyridoxine hydrochloride, thiamine hydrochloride and ascorbic acid;
   (d) an antacid component;
   (e) an electrolyte salt replacing component;
   (f) trace metal ions;
   (g) an antihistamine selected from the group consisting of promethazine-hydrochloride, chlor-phenisamine maleate, diphenhydramine hydrochloride, dimenhydrinate, carboxamine maleate, pyrilamine maleate, tripelennamine hydrochloride or pamoate, brompheniramine maleate, hydroxyzine hydrochloride or lactate, cyclizine hydrochloride or lactate, meclizine hydrochloride or buclizine hydrochloride;
   (h) fructose;
   (i) an alkaloid having a stimulating effect; and
   (j) pharmaceutically acceptable additives according to the form of administration, selected from the group consisting of sweetening agents, flavoring agents, coloring agents, effervescent components, carriers, and fillers.

2. A therapeutic composition for the treatment of the symptoms associated with the excessive intake of alcohol, comprising:
   (a) an analgesic;
   (b) 70 to 1500 mg per unit dose of nicotinamide; and
   (c) 70 to 300 mg of nicotinamide adenine dinucleotide (NAD);
   wherein the amount of components (b) and (c) is 7% or greater by weight of component (a), further comprising one or more of the following components:
   (d) a water soluble vitamin selected from the group consisting of pantothenic acid, riboflavin, pyridoxine hydrochloride, thiamine hydrochloride and ascorbic acid;
   (e) an antacid component;
   (f) an electrolyte salt replacing component;
   (g) trace metal ions;
   (h) an antihistamine selected from the group consisting of promethazine-hydrochloride, chlor-phenisamine maleate, diphenhydramine hydrochloride, dimenhydrinate, carboxamine maleate, pyrilamine maleate, tripelennamine hydrochloride or pamoate, brompheniramine maleate, hydroxyzine hydrochloride or lactate, cyclizine hydrochloride or lactate, meclizine hydrochloride or buclizine hydrochloride;

(i) fructose;

(j) an alkaloid having a stimulating effect; and (k) pharmaceutically acceptable additives according to the form of administration, selected from the group consisting of sweetening agents, flavoring agents, coloring agents, effervescent components, carriers, and fillers.

3. The therapeutic composition according to claim 1, wherein the amount of component (b) is greater than 10% by weight of component (a).

4. The therapeutic composition according to claim 1, wherein the amount of component (b) is from 7% to 10% by weight of component (a).

5. A therapeutic composition according to claims 1 or 2, wherein component (a) is an analgesic selected from the group consisting of diflunisal, sulindac, fenoprofen calcium, acetaminophen, mefenamic acid, naproxen, codeine, dextropropoxyphene HCl, and meperidine.

6. A therapeutic composition according to claims 1 or 2 comprising one or more of said water-soluble vitamins selected from the group consisting of pantothenic acid, riboflavin, pyridoxine hydrochloride, thiamine hydrochloride and ascorbic acid.

7. A therapeutic composition according to claims 1 or 2, comprising an ion selected from the group consisting of sodium, potassium, magnesium or calcium, wherein said ions are salts or chelates.

8. A therapeutic composition according to claims 1 or 2, wherein said trace metal ions are selected from the group consisting of ions of zinc, chromium, manganese, copper and iron.

9. A therapeutic composition for the treatment of the symptoms associated with the excessive intake of alcohol, comprising per dosage units:
600–900 mg of acetylsalicylic acid;
300–500 mg of nicotinamide; and
0.5 to 20 mg of zinc ions.

10. The therapeutic composition according to claim 1, to be administered to an individual before going to sleep comprising components (a), (b), (c) and (h).

11. The therapeutic composition according to claim 2, to be administered to an individual before going to sleep comprising components (a), (b), (c) and (i).

12. The therapeutic composition according to claim 10 or 11 further comprising one or more of the following components:

(d) an antacid component;

(e) an electrolyte salt replacing component;

(f) trace metal ions;

(g) an antihistamine; and (j) pharmaceutical acceptable additives according to the form of administration, selected from the group consisting of sweetening agents, flavoring agents, coloring agents, effervescent components, carriers or fillers.

13. The therapeutic composition according to claim 1 to be administered to an individual the morning after, comprising components (a), (b), (c) and (i).

14. A therapeutic composition according to claim 9 further comprising one or more of the following components:

(d) an antacid component;

(e) an electrolyte salt replacing component;

(f) trace metal ions;

(g) an antihistamine; and (j) pharmaceutical acceptable additives according to the form of administration, selected from the group consisting of sweetening agents, flavoring agents, coloring agents, effervescent components, carriers or fillers.

15. A method for treating the symptoms associated with the excessive intake of alcohol, comprising administering to an individual an effective amount of the therapeutic composition of claim 1.

16. A method for treating the symptoms associated with the excessive intake of alcohol, comprising administering to an individual an effective amount of the therapeutic composition of claim 2.

17. A method for treating the symptoms associated with the excessive intake of alcohol, comprising administering to an individual an effective amount of the therapeutic composition of claim 3.

18. A method for treating the symptoms associated with the excessive intake of alcohol, comprising administering to an individual an effective amount of the therapeutic composition of claim 4.

19. A method for treating the symptoms associated with the excessive intake of alcohol, comprising administering to an individual an effective amount of the therapeutic composition of claim 5.

20. A method for treating the symptoms associated with the excessive intake of alcohol, comprising administering to an individual an effective amount of therapeutic composition of claim 6.

21. A method for treating the symptoms associated with the excessive intake of alcohol, comprising administering to an individual an effective amount of the therapeutic composition of claim 7.

22. A method for treating the symptoms associated with the excessive intake of alcohol, comprising administering to an individual an effective amount of the therapeutic composition of claim 8.

23. A method for treating the symptoms associated with the excessive intake of alcohol, comprising administering to an individual an effective amount of the therapeutic composition of claim 9.

24. A method for treating the symptoms associated with the excessive intake of alcohol, comprising administering to an individual an effective amount of the therapeutic composition of claim 10.

25. A method for treating the symptoms associated with the excessive intake of alcohol, comprising administering to an individual an effective amount of the therapeutic composition of claim 11.

26. A method for treating the symptoms associated with the excessive intake of alcohol, comprising administering to an individual an effective amount of the therapeutic composition of claim 12.

27. A method for treating the symptoms associated with the excessive intake of alcohol, comprising administering to an individual an effective amount of the therapeutic composition of claim 13.

28. A method for treating the symptoms associated with the excessive intake of alcohol, comprising administering to an individual an effective amount of the therapeutic composition of claim 14.

* * * * *